(12) United States Patent
Forget et al.

(10) Patent No.: US 9,393,193 B2
(45) Date of Patent: Jul. 19, 2016

(54) COMPOSITIONS FOR CONTROLLING HEARTWORM INFESTATION

(75) Inventors: Patrick Forget, Merignac (FR); Vassilios Kaltsatos, Libourne (FR); Stephan Warin, Libourne (FR)

(73) Assignee: CEVA SANTA ANIMALE, Libourne (FR)

( * ) Notice: Subject to any disclaimer, the term of this patent is extended or adjusted under 35 U.S.C. 154(b) by 0 days.

(21) Appl. No.: 13/813,259

(22) PCT Filed: Jul. 29, 2011

(86) PCT No.: PCT/EP2011/063102
§ 371 (c)(1),
(2), (4) Date: Mar. 25, 2013

(87) PCT Pub. No.: WO2012/013782
PCT Pub. Date: Feb. 2, 2012

(65) Prior Publication Data
US 2013/0178432 A1 Jul. 11, 2013

Related U.S. Application Data

(60) Provisional application No. 61/369,434, filed on Jul. 30, 2010.

(51) Int. Cl.
*A61K 9/00* (2006.01)
*A01K 13/00* (2006.01)
*A01K 27/00* (2006.01)
*A61K 31/7048* (2006.01)

(52) U.S. Cl.
CPC .............. *A61K 9/0017* (2013.01); *A01K 13/003* (2013.01); *A01K 27/007* (2013.01); *A61K 31/7048* (2013.01)

(58) Field of Classification Search
CPC ................... A61K 31/7048; A61K 9/0017
USPC ............................................. 514/30
See application file for complete search history.

(56) References Cited

U.S. PATENT DOCUMENTS 5,980,496 A 11/1999 Jacobsen et al.
6,426,333 B1 7/2002 Huet et al.

FOREIGN PATENT DOCUMENTS

WO WO 97/026895 7/1997
WO WO 2007/018659 2/2007
WO WO 2012/013791 2/2012

OTHER PUBLICATIONS

Arther, R.G. et al. "Imidacloprid/moxidectin topical solution for the prevention of heartworm disease and the treatment and control of flea and intestinal nematodes of cats" *Veterinary Parasitology*, 2005, pp. 219-225, vol. 133.
McTier, T.L. et al. "Prevention of experimentally induced heartworm (*Dirofilaria immitis*) infections in dogs and cats with a single topical application of selamectin" *Veterinary Parasitology*, 2000, pp. 259-268, vol. 91.
Clark, S.L. et al. "Long-term delivery of ivermectin by use of poly(D,L-lactic-co-glycolic)acid microparticles in dogs" *American Journal of Veterinary Research*, Jun. 2004, pp. 752-757, vol. 65, No. 6.
Cunningham, C.P. et al. "Evaluation of a covered-rod silicone implant containing ivermectin for long-term prevention of heartworm infection in dogs" *American Journal of Veterinary Research*, Sep. 2006, pp. 1564-1569, vol. 67, No. 9.
Moulia-Pelat, J.P. et al. "Advantages of an annual single dose of ivermectin 400 μg/kg plus diethylcarbamazine for community treatment of bancroftian filariasis" *Transactions of the Royal Society of Tropical Medicine and Hygiene*, 1995, pp. 682-685, vol. 89, No. 6.
Written Opinion in International Application No. PCT/EP2011/063102, Jun. 8, 2012, pp. 1-9.

*Primary Examiner* — Layla Berry
(74) *Attorney, Agent, or Firm* — Saliwanchik, Lloyd & Eisenschenk

(57) ABSTRACT

The present invention relates to ivermectin formulations for administration to pet and domestic animals. These formulations provide long term protection against *Dirofilaria* parasites, without the risks for secondary adverse of conventional formulations. Preferred formulations are collars, collar strips, or medallions, attachments for collars, ear tags, bands which are affixed to limbs or parts of the body, adhesive strips and films, and peel-off films, or spot-on or pour-on forms which are administered at least twice a year up to around once a year.

9 Claims, No Drawings

COMPOSITIONS FOR CONTROLLING HEARTWORM INFESTATION

CROSS-REFERENCE TO RELATED APPLICATIONS

This application is the U.S. national stage application of International Patent Application No. PCT/EP2011/063102, filed Jul. 29, 2011, which claims the benefit of U.S. Provisional Patent Application No. 61/369,434, filed Jul. 30, 2010, the disclosures of which are hereby incorporated by reference in their entireties, including all figures, tables and amino acid or nucleic acid sequences.

FIELD OF THE INVENTION

This invention relates an improved antiparasitic composition for controlling heartworm disease infestation in an animal subject. The current invention also provides novel routes of administration and new combinations related to such improved compositions.

BACKGROUND

Heartworm is a parasitic roundworm (especially *Dirofilaria immitis* and *Dirofilaria repens*) that is spread from host to host through the bites of mosquitoes. The definitive host is the dog but it can also infect cats, wolves, coyotes, foxes and other animals, such as ferrets, sea lions and even bovines and humans. The parasite is commonly called "heartworm" because the adult reproductive stage of its life cycle resides primarily in the right ventricle of its host where it can live for many years. Heartworm infection may result in serious disease for the host. When a mosquito bites an infected animal, young heartworms called microfilariae enter into that mosquito's system. Within two weeks, the microfilariae develop into infective larvae inside mosquitoes; these infective larvae can be transmitted to another animal when mosquitoes take their next blood meal. Upon entering the dog's circulatory system, the larvae develop and migrate to the dog's heart where they mature and breed. *Dirofilaria* young, termed "microfilariae," migrate throughout the hosts' circulatory system, where they may be ingested by a mosquito that feeds upon the infected hosts. The *Dirofilaria* life cycle is completed when the ingested microfilariae mature into infective larvae in the mosquito. Development of the larvae into adult worms takes about 180 days in dogs.

*Dirofilaria immitis* presents as white threadlike round worms reaching up to 20 cm for adult males (12-20 cm) and 31 cm for adult females (25-31 cm), with a mean diameter of 1 mm. They are characterised by a relatively smooth cuticle. Heartworms are primarily found in the pulmonary artery in dogs with low parasitic burden (<50 worms). In infestations with high parasitic burden (>50 worms), they may reach the right ventricle, right atrium, and occasionally vena cava. The initial response includes swelling of small pulmonary arteries and blood clotting. The physical presence of the heartworm parasite in the pulmonary artery and right ventricle of the canine heart, and the resulting destruction of tissue, causes respiratory and circulatory problems which can be fatal under conditions of stress or vigorous exercise. Pulmonary hypertension and right-sided congestive heart failure may result. Because it takes a large number of heartworms to clog up blood flow to a significant degree, heartworms can be present inside the heart for up to 2 or 3 years before causing clinical signs. As the disease progresses, lung tissue can be destroyed leading to a worsening cough and liver and kidney damage can occur due to reduced blood flow to these organs. If left untreated, heartworm disease may result in death. After adult heartworms mate and produce immature heartworms, an infected dog which is bitten by an uninfected mosquito will transmit microfilariae to the mosquito, beginning the cycle again. The life cycle of the heartworm is approximately 6 months. The heartworm parasite has also been shown to be the cause of focal lung, liver, eye and cutaneous lesions in man (Hamilton, R. G., et al., Exper. Parasitol., 56:298-313 (1983)).

Heartworm disease due to *Dirofilaria immitis* and/or *Dirofilaria repens* continues to cause severe disease and even death in dogs and other animals (cats, bovines, humans, guinea porcine and ferrets) in many parts of the world, even though safe, highly effective and convenient preventatives have been available for the past two decades. Moreover, the parasite and vector mosquitoes continue to spread into areas where they have not been reported previously. The control of such parasites has long been recognized as an important aspect of human and animal health regimens. Although a number of alternatives to control infestation are in use, these suffer from a variety of problems, including a limited spectrum of activity, the need for repeated treatment (lack of compliance) and, in some rare instances, resistance by parasites.

Currently for curative treatment, only two arsenic derivatives are available for clinically infested dogs, namely thiacetarsamide (Caparsolate® marketed by Abbott laboratories) which is an old medication, with severe adverse effects and melarsomine dihydrochloride (Immiticide® marketed by Merial), which is a more recent drug with fewer side effects.

For chemoprophylaxis, two alternatives are possible to prevent heartworm isease in dogs: daily administration of diethylcarbamazine citrate, or monthly administration of macrocyclic lactones.

Number of macrocyclic lactones have commercialized, for example ivermectin under the name of Ivomec® or Heartgard® marketed by Merial, doramectin (Dectomax marketed by Pfizer Animal Health), moxidectin and abamectin (Avomec®, marketed by Merial).

Also, a slow release formulation of subcutaneously injected moxidectin-impregnated lipid microspheres, providing single dose continuous protection in excess of six months, has been marketed by Fort Dodge under the name of Moxidectin SR®, ProHeart 6® or Guardian SR®. However, this product was voluntarily removed from the US market in September 2004 for issues related to safety, and currently has been allowed once again by FDA under a risk minimization and restricted distribution program.

Ivermectin consists of a mixture of two homologous compounds, 22,23-dihydroavermectin B1a (H2B1a, not less than 80%) and 22,23-dihydroavermectin B1b (H2B1b, not more than 20%) as described in U.S. Pat. No. 4,199,569. The invention relates to use of said mixture.

Ivermectin has been marketed for treatment of various helminth intestinal parasites including heartworm in animals. Currently approved Heartgard® chewable tablets are administered orally at monthly intervals at the recommended minimum dose level of 6.0 mcg of ivermectin per kilogram (2.72 mcg/lb) of body weight. Heartgard® is available in three dosage strengths for dogs of different weights (68, 136 and 272 mcgs). For other species like swine, cattle, sheep, and horse, ivermectin is available in 10 mg/ml and 2.7 mg/ml injectable form; 0.153 percent and 1.87 percent paste form; 10 mg/ml liquid oral form.

High plasma total ivermectin concentrations are however considered a risk factor for diseases of the nervous systems in dogs. In a 36-clay study in beagle dogs in which ivermectin was administered orally at 0.5 and 2.0 mg/kg of body weight (bw), the concentrations of H2B1a in plasma increased dramatically between days two and eight and reached steady-state after about three weeks. A four-fold increase in the dose resulted in an average eight-fold increase in plasma levels. Such high plasma levels have been observed to cause adverse effects in dogs. In beagle dogs, mydriasis was the most sensitive indicator of toxicity. More severe signs included ataxia and tremors. Deaths were preceded by a comatose state. Approximately 30% of collie dogs were highly sensitive to ivermectin (as estimated from reports from non recommended use of the drug). In a 14-week oral study in beagle dogs (4/sex/group), mydriasis and slight weight loss were observed at 1.0 and 2.0 mg/kg bw. Four dogs in the 2.0 mg/kg bw group developed tremors, ataxia, anorexia and dehydration and were killed prior to the end of the study. The No Observable Effect Levels (NOEL) was 0.5 mg/kg bw. It is now reported that collies are the most frequently affected dogs.

It is known, in humans and in several animal species, that altered expression or function of p-glycoprotein could conceivably allow elevation of brain concentrations of ivermectin and produce severe neurotoxicity. As a consequence of normal dosing regimen for ivermectin, the treated animals necessarily receive a relatively large quantity of the drug which is to remain effective for an extended period. This in turn means that shortly after treatment the animal has a very high concentration of ivermectin in his bloodstream, with this concentration tailing off during the remainder of the period.

Further the currently marketed ivermectin formulations come with certain precautions for usage. The American Heartworm Society (AHS) recognizes the safety-net (or reach-back effect) and adulticidal properties of some macrocyclic lactones, particularly ivermectin. However, heartworm-positive working dogs might be more at risk to develop severe thromboembolism and death. Worsened radiographic and echocardiographic images with greatly restricted exercise suggest that such treatment is contraindicated. Furthermore, even in asymptomatic dogs, it should be administered only with much caution and with examination by a veterinarian at least once every 4-6 months. Likewise, ivermectin must be used with caution in collies and related shepherd dogs that are more susceptible to its neurotoxic effects than other dog breeds.

Accordingly, in order to overcome the foregoing problems, to increase the effectiveness of avermectin in eradication of heartworms, and to provide for more predictable performance of this drug, there is a need in the art for a dosage form which affords improved absorption and bioavailability of averrnectin and more precisely of ivermectin at a lower maximum plasma concentration.

Further the present invention aims to provide novel formulations that are easier to administer and are able to maintain the effective plasma concentration over a prolonged period of time of at least 6 months up to at least 12 months. Generally topical applications are desirable since many formulations are acceptably safe when used topically, but not when used internally. However, developments of various topical pharmaceutical formulations have posed a number of drawbacks. Some formulations require a large volume to be applied to the animal. This can cause considerable mess and can lead to an unpleasant smell. Additionally, if the dosage of a topical formulation is in a large volume, it can be easily shaken off by the animal, thereby reducing the effectiveness of the formulation. Also, when the animal is a house pet, there is a further complication in that the formulation should be safe for human contact. It should also not lead to staining of furniture, carpeting and the like. Finally, even if safe, topical formulations should not be irritating or lead to rashes, hair loss or exhibit other unpleasant side effects.

SUMMARY OF THE INVENTION

There is therefore a need for an improved formulations for the control and/or the treatment of endoparasites and ectoparasites that overcome drawbacks of the prior art. The present invention provides herein such improved formulations, especially suitable for topical application, most preferably as collars, collar strips, medallions, attachments for collars, ear tan, bands which are affixed to limbs or parts of the body, adhesive strips and films, and peel-off films, or spot-on or pour-on form that are capable of delivering ivermectin alone or in association with at least one ectoparasitic or endoparasitic agent, thereby providing long term efficient activity against endo- and/or ectoparasites for at least 6 to 12 months.

The present invention further relates to ivermectin, most preferably formulated as a collar, a collar strip, a medallion, and attachments for collars, ear tags, bands which are affixed to limbs or parts of the body, adhesive strips and films, or peel-off films, or spot-on or pour-on form for administration of pet and domestic animals. These improved formulations achieve effective plasma levels faster and at lower concentrations of the drug, are stable on storage, and exhibit cutaneous tolerability as well as good transdermal delivery characteristics. Also, these formulations provide long term protection against parasites, for at least 6 months up to 12 months without the risks for secondary adverse effects of conventional formulations. Preferred formulations are collars, collar strips, or medallions which are administered at least twice a year up to once a year.

The present invention provides a method of controlling heartworm infestation such as for example dirofilariosis, comprising administering to an animal subject a composition comprising an effective dose of ivermectin to achieve a reduction in *Dirofilaria immitis* and/or *Dirofilaria repens* infestations, wherein said ivermectin composition is administered topically a least twice a year up to around once a year.

The present invention provides an improved method of controlling heartworm infestation by administering a protective dose of an avermectin sufficient to achieve a reduction in *Dirofilaria immitis* and/or *Dirofilaria repens* in a subject, at a lower plasma concentration of avermectin as compared to plasma avermectin concentration obtained via conventional avermectin formulations.

The present invention further provides avermectin formulations having significant parasiticidal activity for controlling heartworm infestation, at a lower plasma concentration when compared to the conventional avermectin formulations. These formulations are safe to use and avoid many common deleterious side effects of conventional formulations.

The present invention still further provides topical formulations that contain an effective dose of an avermectin which can be effective to control the heartworms infestation. The compositions derived herein can also be useful to improve the speed of result and decrease the reoccurrence, compared to other formulations. Preferably, the collars, collar strips or medallions comprise an effective or protective dose of ivermectin.

The topical formulations according to the present invention may be in the form of a collar, a collar strip, a medallion, attachments for collars, ear tags, bands which are affixed to limbs or parts of the body, adhesive strips and films, peel-off films, or spot-on or pour-on form.

The formulations according to the present invention, i.e., collars, collar strips, or medallions may be administered at least twice a year up to once a year.

The present invention still further provides an antiparasitic combination, comprising an effective dose of an avermectin such as ivermectin for controlling *Dirofilaria immitis* and/or *Dirofilaria repens* infestation alone or in association with at least one ectoparasitic or endoparasitic (control) agent.

DETAILED DESCRIPTION

Definitions

As used herein avermectins refer to the most potent anthelmintic, insecticidal and acaricidal compounds known. Several avermectins have been developed, including, ivermectin, abamectin, doramectin, eprinomectin and selamectin. Ivermectin is preferably used in the compositions, topical formulations and methods according to the present invention.

"Conventional avermectin formulations" refers to Heartgard® chewable tablets marketed by Merial, Heartgard® 10 mg/ml and 2.7 mg/ml injectable form; 0.153 percent and 1.87 percent paste form and 10 mg/ml liquid oral form.

"Subject" or "animal subject" refers to any animals able to develop pathologies related to heartworms such as, for example, pet animals. Canines may be the preferred subjects of the present invention. The subject is typically a non-human mammal, and may be any such animal mentioned herein.

"Heartworms" generally may include roundworms that typically reside within the heart of a host during the final reproductive stages of its life cycle. Some specific heartworms may include *Dirofilaria immitis* and *Dirofilaria repens* and any other similar worms of the same class or subclass.

"Combination" as used herein broadly may include two or more elements or compounds physically, chemically, and/or otherwise suitably coupled with each other to produce a desired result. Both components of the combination may be administered simultaneously or sequentially and may be separate dosage forms or may be part of same dosage form.

"Controlling" as used herein broadly include the reduction, the treatment, the eradication and/or the prevention of *Dirofilaria immitis* and *Dirofilaria repens* and any other similar worms of the same class or subclass.

The present invention thus aims at developing improved formulations of an avermectin, particularly ivermectin, that overcome the disadvantages and constrains of existing treatment a provides a method of treatment and/or controlling infestation, and dosage regimen and formulations that can be easily and safely administered to produce an efficacious response across many species susceptible to heartworm infection.

Currently approved dosages of ivermectin are about 6 mcg/kg orally or 200 mcg/kg subcutaneously. It is generally reported that ivermectin administered per se at 6 mcg/kg is able to kill efficiency one month aged *Dirofilaria* larvae. Cunningham C P et al., (Am. J. Vet. Res., 2006, 67) brought evidence that this effective rate might be superior or equal to 0.2 ng/mL of ivermectin in the plasma.

The background art does not teach or suggest a method or formulation of ivermectin, providing a lower effective concentration of the active ivermectin drug relative to that resulting from the administration of conventional ivermectin formulations, whilst maintaining the efficacy and exhibiting improved safety profile. The applicant has surprisingly established an effective rate at around 0.1 ng/mL of ivermectin in the plasma. Thus, the formulations according to the present invention provide a long term protection, e.g., at least 6 months for the collar, strip collar, or medallion formulation against infections caused by parasites.

Accordingly in a preferred embodiment, the current invention provides a method of controlling heartworm infestation by administering a therapeutically effective or protective dose of ivermectin which achieves a reduction in *Dirofilaria immitis* and/or *Dirofilaria repens* in an animal subject, at a lower plasma concentration of ivermectin as compared to plasma ivermectin concentration obtained via conventional ivermectin formulations as defined by Cunningham C P et al. (Am. J. Vet. Res., 2006, 67). In a preferred embodiment, said lower plasma ivermectin concentration is less than 0.2 ng/mL, or less to 0.15 ng/mL, ranges from 0.1 ng/mL to 0.15 ng/mL, or is about 0.1 ng/mL. In another preferred embodiment said lower plasma ivermectin concentration is about 5-95% of conventional ivermectin formulations, particularly preferred plasma concentration is about 50% of conventional ivermectin formulations.

In another embodiment, the present invention provides a composition for controlling heartworm infestation in a subject, wherein the composition is effective at a lower plasma concentration of ivermectin as compared to conventional ivermectin formulations, and exhibits a reduced side effect profile as compared to a conventional formulation. In a preferred embodiment, said lower plasma ivermectin concentration is less than 0.2 ng/mL, or less to 0.15 ng/mL, ranges from 0.1 ng/mL to 0.15 ng/mL, or is about 0.1 ng/mL. In another preferred embodiment said lower plasma ivermectin concentration is about 5-95% of conventional ivermectin formulations, particularly preferred plasma concentration is about 50% of conventional ivermectin formulations.

The present invention also provides novel active composition for controlling *Dirofilaria immitis* and/or *Dirofilaria repens* infestation in subject, comprising a combination of an avermectin, preferably ivermectin and at least one other ectoparasitic or endoparasitic (control) agent. Said composition may be administered and used in the manner described herein for other compositions, including the dosage, time period or topical form.

The formulations of the present invention are preferably administered via shaped articles. Shaped articles are, inter alfa, collars, collar strips, medallions, pumps, attachments for collars, ear tags, bands which are affixed to limbs or parts of the body, adhesive strips and films, peel-off films or spot on or pour-on forms.

When compared to the existing treatment options, e.g., chewable s, which are administered monthly, injectable suspensions which a long term action, i.e., 6-12 months, the present topical formulations has the advantage of being easily applied, not being invasive, does not contain any aggressive solvent, and has a long duration of action. Also, treatment may be easily discontinued in certain rare cases, like for example if there is any issue of toxicity, incompatibility with another treatment or surgery, which cannot be done in case of an injected product. Preferably, the formulations according to the present invention are administered to the animal subjects at least twice a year and up to once a year.

Furthermore, the collars of the present invention are novel when compared to the other marketed collars, strips, or medallions, in the sense that the latter only contain external anti-parasites, but lack an active controlling infestation agent such as an avermectin, and preferably ivermectin, having a systemic action and/or an agent active against internal parasites.

The compositions of the present invention may be in the form of collars, collar strips, or medallions, attachments for collars, ear tags, bands which are affixed to limbs or parts of the body, adhesive strips and films, peel-off films, or spot-on and pour-on form comprising an amount of ivermectine sufficient to achieve a plasma concentration of less than 0.2 ng/mL, or less to 0.15 ng/mL, ranging from 0.1 ng/mL to 0.15 ng/mL, or about of 0.1 ng/mL for a period of at least 6 months up to 12 months.

To produce collars, strips or medallions, polyvinyl resins, polyurethanes, polyacrylates, epoxy resins, cellulose, cellulose derivatives, polyamides and polyesters are used in known manner, and these are sufficiently compatible with avermectin and particularly ivermectin. The polymers should have sufficient strength and pliability so as not to tear or become brittle when shaped into a band. They must be sufficiently long-lasting so as to be resistant to normal wear and tear. In addition, the polymers must allow the active ingredients to migrate satisfactorily to the surface of the moulded collar. These requirements are fulfilled in particular by solid polyvinyl resins, i.e., polymerisation products formed by polymerisates of a vinyl double bond. Typical vinyl resins are, for example, polyvinyl halides, such as polyvinyl chloride, polyvinyl chloride-vinyl acetate and polyvinyl fluoride; polyacrylater and polymethacrylate esters, such as polymethyl acrylate and polymethyl methacrylate; and polyvinylbenzenes, such as polystyrene and polyvinyltoluene.

Appropriate plasticizers may be used for making collars, collar strips or medallions. Which plasticizer is to be used depends on the resin and its compatibility with the plasticizer. Suitable plasticizers are, for example, hydrogenated castor oil, octyl dodecanol, vegetable oils (ie coconut oil ... ), esters of phosphoric acid, such as tricresyl phosphate, esters of phthalic acid, such as dimethyl phthalate and dioctyl phthalate, and esters of adipic acid, such as diisobutyl adipate. Other esters may also be used, such as the esters of azelaic acid, maleic acid, ricinoleic acid, myristic acid, palmitic acid, oleic acid, sebacic acid, stearic acid and trimellitic acid, as well as complex linear polyesters, polymeric plasticizers and epoxidised soy bean oils. The amount of plasticizer is about 10 to 50% by weight, preferably 20 to 45% by weight, of the total composition.

The collars, collar strips, or medallions, attachments for collars, ear tags, bands which are affixed to limbs or parts of the body, adhesive strips and films, and peel-off films may also contain further constituents, such as stabilizers, lubricants, fillers and colorants, without changing the underlying properties of the composition.

Suitable stabilizers are antioxidants and agents which protect the collars, collar strips, or medallions from ultraviolet radiation and undesired degradation during processing, such as extrusion. A few stabilizers, such as epoxidised soy bean oils, additionally serve as secondary plasticizers.

The lubricants used may be, for example, oils, waxes, stearates, stearic acid and polyethylenes of a low molecular weight.

Colorants are all colorants which are licensed for use on animals and which can be dissolved or suspended. Adjuvants are also spreading oils such as isopropyl myristate, dipropylene glycol pelargonate, silicone oils, fatty acid esters, triglycerides and fatty alcohols. Antioxidants are sulphites or metabisulphites such as potassium metabisulphite, ascorbic acid, butylhydroxytoluene, butylhydroxyanisole and tocopherol.

The choice of processing method in the production of the collars, collar strips, or medallions according to the invention depends on a technical basis on the rheological properties of the collar material and the shape of the desired collar. The processing method may be adjusted according to the processing technology or according to the type of shaping. In the processing technology, the processes may be classified according to the continuous rheological conditions therein.

According to these, for viscous collar materials pouring, pressing, injecting and coating may be considered, and for elastoviscous polymers injection moulding, extrusion, calendering, rolling and optionally edging may be considered. When classified according to the type of shaping, the moulded collars according to the invention may be produced by pouring, immersion, pressing, injection-moulding, extrusion, calendering, stamping, bending, cupping, etc.

Preferred collars, collar strips, medallions, attachments for collars, ear tags, bands which are affixed to limbs or parts of the body, adhesive strips and films, and peel-off films may be composed of a polymer matrix comprising ethylene/vinyl acetate (EVA) copolymer blended with a polyether block amide (PEBAX). The polymer matrix being charged in the active composition with a ratio by weight of less than 0.66. The collars, strips, medallions etc., so obtained may be administered or applied to the animal subject as a fit-on, so as to ensure close contact between the hair of the animal subject and the present formulation and subsequent penetration of ivermectin, as the endoparasiticide in the bloodstream of the animal.

According to another embodiment the ivermectin may be delivered by a device that applies a predefined specific dose of ivermectin at one or more time points to the skin of the animal. The ivermectin is not administered continuously by the device, and preferably is administered at time points in accordance with those described herein for administration of ivermectin. The device is typically fixed to the animal and is preferably incorporated into any of the delivery means mentioned herein, such as a collar. The device preferably comprises a minipump which delivers the ivermectin from a store of ivermectin to the skin of the animal. The device may comprise a controlling means which is capable of operating the minipump to administer the ivermectin at the required times.

According to the present invention, collars, collar strips, medallions, attachments for collars, ear tags, bands which are affixed to limbs or parts of the body, adhesive strips, films, and peel-off films dosage forms may be administered at a single time (e.g., as one dose) or at separate time points (e.g., as divided doses). When the dosage form is administered at separate time points, the interval between the separate administrations of the divided dose may be from several months, preferably every 6 months to at least 12 months. Indeed, the administration of ivermectin for example in a collar, collar strip, or medallion provides a long term protection against parasites for a period of at least 6 months to around 12 months.

In an additional preferred embodiment, the compounds in these amounts be combined with other ectoparasitic or endoparasitic control agents.

In a particularly embodiment, the present invention provides a kit useful in the control of heartworm infestation in a subject, which comprises a dose of ivermectin which achieves a reduction or control of infestation of *Dirofilaria immitis* and/or *Dirofilaria repens* in animal subjects, at a lower plasma concentration of ivermectin as compared to plasma ivermectin concentration obtained via conventional ivermectin formulation, optionally in combination with ectoparasitic (ticks, fleas) or endoparasitic (*Ascaris, Ancylostoma*), optionally a carrier, and instructions for the treatment of a parasitic infestation.

EXAMPLES

Example 1

Preparation and Testing of Collars Containing Ivermectin

The following two types of collar containing 0.45% of invermectin as listed in the following Table 1 were prepared.

TABLE 1

| Constituents | Collar 0.45% |
|---|---|
| Ivermectin | 0.45 |
| Pebax (Polyamide) | 60 |
| EVA PA 538 | 25 |
| Isopropanol | 0.75 |
| Coconut oil | 4.8 |
| Soft-n-safe (hydrogenated castor oil) | 4.5 |
| Eutanol G (octyl dodecanol) | 4.5 |
| Total | 100 |

For the tests, 2 adult dogs have received a collar of 0.45% for at least 120 days. The concentrations of ivermectin in the plasma, collected in the jugular vein at day 0 (D0) to day 120 (D120), from each groups are presented in Table 2 in ng/mL.

TABLE 2

| | Dogs with Collar 0.45% | | | |
|---|---|---|---|---|
| | Ivermectin (ng/mL) | | | |
| Days | Dog 1 | Dog 2 | Average | Standard deviation |
| 0 | 0.250 | 0.115 | 0.183 | 0.095 |
| 2 | 0.530 | 0.472 | 0.501 | 0.041 |
| 4 | 0.286 | 0.313 | 0.300 | 0.019 |
| 10 | 0.229 | 0.162 | 0.196 | 0.047 |
| 15 | 0.272 | 0.168 | 0.220 | 0.074 |
| 30 | 0.159 | 0.230 | 0.195 | 0.050 |
| 42 | 0.121 | 0.330 | 0.226 | 0.148 |
| 71 | 0.248 | 0.423 | 0.336 | 0.124 |
| 99 | 0.347 | 0.817 | 0.582 | 0.332 |
| 120 | 0.391 | 0.334 | 0.363 | 0.040 |
| 180 | 0.200 | 0.150 | 0.175 | 0.025 |
| 365 | 0.150 | 0.115 | 0.132 | 0.018 |

Example 2

Dirofilariosis Infestation Test

For the tests, 7 adult dogs are divided, into two groups: one group of 4 dogs receives an ivermectin collar as described in Example 1 and the second control group of 3 dogs does not receive any treatment.

These 7 dogs are challenged by a subcutaneous injection of 2 mL of 75 *Dirofilaria immitis* L3 larvae at 120 days (D120), after first wearing the collars.

*Dirofilaria immitis* infestations are evaluated by serological tests done by Elisa detection test of *Dirofilaria immitis* (Canine Heartworm Antigen Test Kit, PetChek™ HTWM PF-Idexx) 150 days (D270), 195 days (D315) or 240 days (D360) after the *dirofilaria* challenge (D120).

The D315 and D360 serological test are realized after removing the collar at D150 days. The necropsy of the control dogs showed that half of the worms were in the lung artery, and half in the heart.

Infestation results demonstrate no *Dirofilaria immitis* infestation of the dogs which receive with the collar of Example 1, at D270, D315 and D360 post challenge.

The invention claimed is:

1. A method of controlling heartworm infestation in a dog, the method comprising applying to the dog a topical device containing a composition comprising an effective dose of ivermectin, wherein said topical device is applied for a period of at least 6 months to about 12 months to said dog and the topical device delivers and maintains an average plasma concentration of ivermectin in the dog between 0.132 ng/ml, and 0.582 ng/mL during the application period, said application leading to a control of *Dirofilaria immitis* or *Dirofilaria repens* infestation in said dog.

2. The method of claim 1, wherein the topical device is selected from a collar, collar strip, medallion, attachment for collar, an ear tag, a band which is affixed to limbs or other parts of the body, an adhesive strip or film, or a peel-off film, spot-on or pour-on form.

3. A topical veterinary drug composition for use in controlling heartworm infestation in a dog, wherein said composition is in the form of a shaped topical article selected from a collar, collar strip, medallion, an attachment for a collar, ear tag, bands which are affixed to limbs or parts of the body, adhesive strip or film, and peel-off film, and wherein said composition delivers ivermectin according to the following profile:

| Days | Average Ivermectin concentration ng/mL of plasma |
|---|---|
| 0 | 0.183 |
| 2 | 0.501 |
| 4 | 0.300 |
| 10 | 0.196 |
| 15 | 0.220 |
| 30 | 0.195 |
| 42 | 0.226 |
| 71 | 0.336 |
| 99 | 0.582 |
| 120 | 0.363 |
| 180 | 0.175 |
| 365 | 0.132. |

4. The composition of claim 3, wherein said composition further comprises another ectoparasitic or endoparasitic agent.

5. A kit for treating or preventing parasitic infestation of heartworm in a dog, which comprises a shaped topical article selected from a collar, collar strip, medallion, an attachment for a collar, ear tag, bands which are affixed to limbs or parts of the body, adhesive strip or film, and peel-off film, comprising an effective dose of ivermectin for control of *Dirofilaria immitis* or *Dirofilaria repens* infestation, wherein said article delivers ivermectin to said dog to maintain ivermectin concentration according to the following profile:

| Days | Average Ivermectin concentration ng/mL of plasma |
|---|---|
| 0 | 0.183 |
| 2 | 0.501 |
| 4 | 0.300 |
| 10 | 0.196 |

-continued

| Days | Average Ivermectin concentration ng/mL of plasma |
|---|---|
| 15 | 0.220 |
| 30 | 0.195 |
| 42 | 0.226 |
| 71 | 0.336 |
| 99 | 0.582 |
| 120 | 0.363 |
| 180 | 0.175 |
| 365 | 0.132. |

6. The kit of claim 5, which further comprises an ectoparasitic or endoparasitic control agent optionally with a carrier.

7. A method for treating or preventing heartworm infestation in a dog, the method comprising applying to said dog a topical device selected from a collar, collar strip, medallion, attachment for collar, an ear tag, a band which is affixed to limbs or parts of the body, an adhesive strip or film, and a peel-off film, containing a composition comprising an effective dose of ivermectin, wherein said topical device is applied to said dog for a period of 6 months to 12 months, and the topical device delivers ivermectin to said dog at a rate so as to maintain the concentration of ivermectin according to the following profile:

| Days | Average Ivermectin concentration ng/mL of plasma |
|---|---|
| 0 | 0.183 |
| 2 | 0.501 |
| 4 | 0.300 |
| 10 | 0.196 |
| 15 | 0.220 |
| 30 | 0.195 |
| 42 | 0.226 |

-continued

| Days | Average Ivermectin concentration ng/mL of plasma |
|---|---|
| 71 | 0.336 |
| 99 | 0.582 |
| 120 | 0.363 |
| 180 | 0.175 |
| 365 | 0.132. |

8. A kit for treating and/or preventing parasitic infestation of heartworm in a non-human animal subject, which comprises a collar containing a formulation comprising an effective dose of ivermectin, wherein said formulation has the following composition by % weight:

| | |
|---|---|
| Ivermectin | 0.45 |
| Pebax (Polyamide) | 60 |
| EVA PA 538 | 25 |
| Isopropanol | 0.75 |
| Coconut oil | 4.8 |
| Soft-n-safe (hydrogenated castor oil) | 4.5 |
| Eutanol G (octyl dodecanol) | 4.5 | the kit further comprising instructions for the treatment and/or prevention of heartworm infestation in said animal.

9. A collar containing a formulation having the following composition by % weight:

| | |
|---|---|
| Ivermectin | 0.45 |
| Pebax (Polyamide) | 60 |
| EVA PA 538 | 25 |
| Isopropanol | 0.75 |
| Coconut oil | 4.8 |
| Soft-n-safe (hydrogenated castor oil) | 4.5. |

* * * * *